United States Patent [19]

Rienstra et al.

[11] Patent Number: 5,045,456
[45] Date of Patent: Sep. 3, 1991

[54] PROCESS FOR REMOVING BACTERIAL ENDOTOXIN FROM GRAM-NEGATIVE POLYSACCHARIDES

[75] Inventors: Mark S. Rienstra; Edgar M. Scattergood, both of Lansdale, Pa.

[73] Assignee: Merck & Co., Inc., Rahway, N.J.

[21] Appl. No.: 595,722

[22] Filed: Oct. 9, 1990

Related U.S. Application Data

[63] Continuation of Ser. No. 364,927, Jun. 12, 1989, abandoned.

[51] Int. Cl.$^5$ .................. C12P 19/04; C12P 1/04; C12R 1/21
[52] U.S. Cl. .................... 435/101; 210/601; 210/616; 210/631; 424/88; 424/92; 435/170; 435/262; 435/280; 435/800; 435/803; 435/851; 536/1.1
[58] Field of Search ............... 435/101, 170, 262, 280, 435/800, 803; 536/1.1; 210/601, 616, 631; 424/88, 92

[56] References Cited

U.S. PATENT DOCUMENTS

| | | | |
|---|---|---|---|
| 4,196,192 | 4/1980 | Kuo | 424/92 |
| 4,220,717 | 9/1980 | Kuo | 435/101 |
| 4,474,758 | 10/1984 | Kuo et al. | 424/88 |
| 4,695,624 | 9/1987 | Marburg et al. | 424/92 |

OTHER PUBLICATIONS

Sweadner et al., App. Environ. Micro. 34: 382-385 (1977).
Sands and Chun, J. Biol. Chem. 255: 1221-1226 (1980).
McIntire, et al., Biochem. 8: 4063-4066 (1969).
Ribi et al., J. Bact. 92: 1493-1509 (1966).
Feldstine et al., J. Parenter. Drug Assoc. 33: 125-131 (1979).
Berman et al., J. Parenter. Sci. Technol. 41: 158-163 (1987).
Henderson and Beans, Kidney Internatl. 14: 522-525 (1978).
Nelsen, Pharm. Technol. 2: 46-80 (1978).
Gerba et al., Pharm. Technol. 4: 83-89 (1980).
Hou et al., App. Environ. Micro. 40: 892-896 (1980).
Robinson et al., Parneternal Drug Assoc. Philadelphi, pp. 54-69 (1985).
Berger et al., Adv. Chem. Ser. 16: 168-197 (1956).
Gemmell et al., Pharm. J. 154: 126 (1945).
Brindle and Rigby, Pharm. J. 157: 85-86 (1946).
Sawada et al., Appl. Environl. Micro. 51: 813-820 (1986).
Gerba et al., Appl. Environl. Micro. 50: 1375-1377 (1985).
Nolan et al., Proc. Soc. Exptl. Biol. Med. 149: 766-770 (1975).

*Primary Examiner*—Herbert J. Lilling
*Attorney, Agent, or Firm*—Hesna J. Pfeiffer; Richard S. Parr

[57] ABSTRACT

A process for removing endotoxin from Gram-negative polysaccharides such as *H. influenzae* polyribosylribitol phosphate by adding alcohol incrementally until substantially all lipopolysaccharide precipitates.

5 Claims, 3 Drawing Sheets

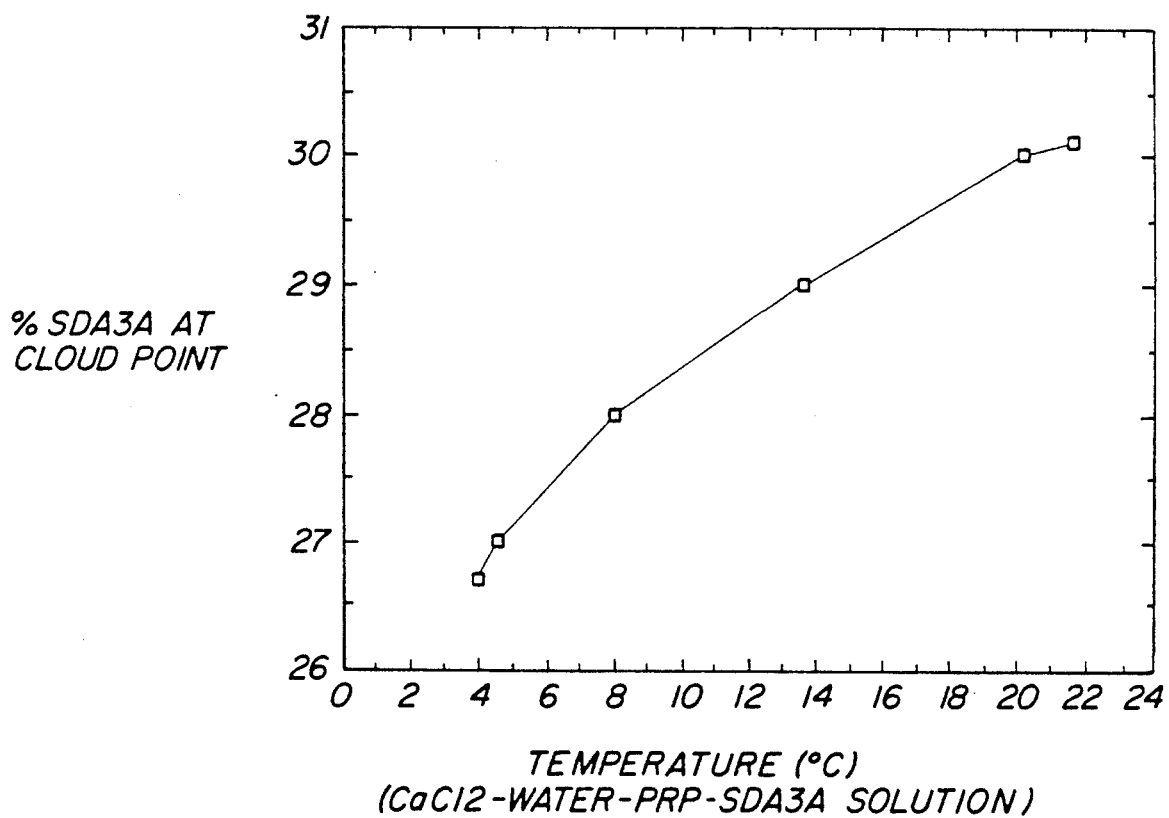

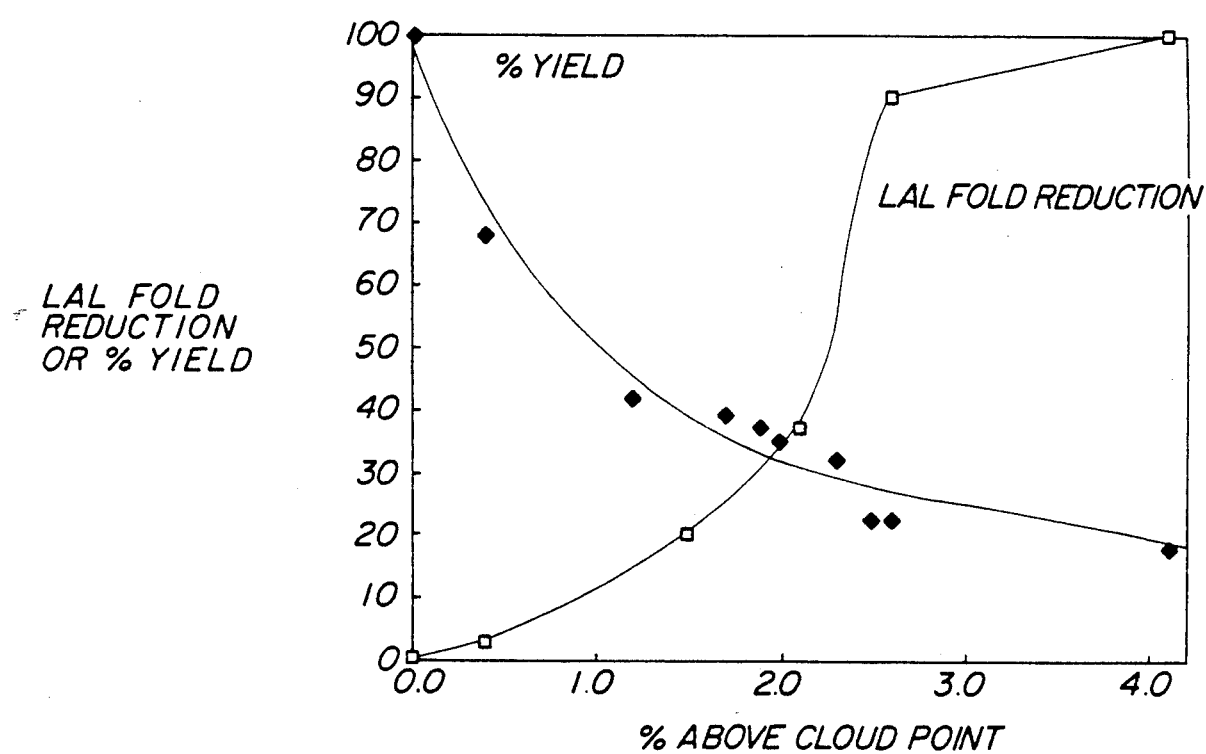

PROCESS FOR REMOVING BACTERIAL ENDOTOXIN FROM GRAM-NEGATIVE POLYSACCHARIDES

This is a continuation of application Ser. No. 364,927, filed June 12, 1989, now abandoned.

BACKGROUND OF THE INVENTION

The invention is a process for removing bacterial endotoxin from gram negative polysaccharides.

Bacterial endotoxin is a potent pyrogen that can often produce fever reactions when administered to patients. Endotoxin is an integral component of the outer cell surface of Gram-negative bacteria. It exists in its natural state as a complex with lipid, carbohydrate and protein. When highly purified, endotoxin does not contain protein, and by its chemical composition is referred to as a lipopolysaccharide (see Weary and Pearson, *Bio. Pharm.* April (1988) pp. 22-29).

The outer-wall layer of Gram-negative bacteria serves as an outer barrier through which materials must penetrate if they are to reach the cell; it is selectively permeable. Generally, endotoxin is released in large amounts only when the cell wall is lysed.

Removal of contaminating endotoxin from Gram-negative polysaccharides is important when the polysaccharide is to be administered to humans. Endotoxins in large quantities can cause shock, severe diarrhea, fever and leukopenia followed by leukocytosis, and can elicit the Shwartzman and Sanarelli-Shwartzman phenomena.

U.S. Pat. No. 4,695,624 describes covalently-modified polyanionic bacterial polysaccharides, stable covalent conjugates of these polysaccharides with immunogenic proteins, and methods of preparing the polysaccharides and conjugates and of confirming covalency. The patent describes purification of the polysaccharide in Example 1, beginning in column 14. After fermentation, inactivation and cell removal, the resulting product undergoes a series of cold ethanol fractionations. Following phenol extraction are diafiltration, ethanol precipitation, ultracentrifugation in ethanol, and collection of the finished product.

Frequently, the amount of contaminating endotoxin remaining after the above-described procedure is higher than desired.

Methods for removing endotoxin which are known in the art are described by Weary and Pearson (ibid): rinsing with nonpyrogenic solution (Feldstine et al., *J. Parenter. Drug Assoc.*, 33, p. 125 (1979) and Berman et al., *J. Parenter. Sci. Technol.*, 41, p. 158 (1987); distillation; ultrafiltration using membranes rated by molecular weight exclusion (Sweadner et al., *Appl. Environ. Microbiol.*, 34, p. 382 (1977) and Henderson et al., *Kidney Int.*, 14, p. 522 (1978); reverse osmosis using thin cellulose acetate or polyamide materials (Nelson, *Pharm. Technol.*, 2, p. 46 (1978); electrostatic attraction (Gerba et al., *Pharm Technol.*, 4, p. 83 (1980) and Hou et al., *Appl. Environ. Microbiol.*, 40, p. 892 (1980); hydrophobic attraction using aliphatic polymers (Robinson et al., in *Depyrogenation* (Parental Drug Association, Philadelphia (1985), pp. 54-69); adsorption using activated carbon (Berger et al., *Adv. Chem. Ser.*, 16, p. 169 (1956), Gemmell et al., *Pharm J.*, 154, p. 126 (1945), and Brindle et al., *Pharm J.*, 157, p. 85 (1946); and affinity chromatography (Soter, *Bio/Technology*, 12, p. 1035 (1984).

Sawada, et al., *Applied and Environmental Microbiology*, April 1986, pp. 813-820, describe removal of endotoxin from water by microfiltration through a microporous polyethylene hollow-fiber membrane. Gerba et al., *Applied and Environmental Microbiology*, December 1985, pp. 1375-1377, describe endotoxin removal from various solutions using charged nylon and cellulose-diatomaceous earth filters. Nolan et al., *Proceedings of the Society for Experimental Biology and Medicine*, Vol. 149, pp. 766-770 (1975), describe endotoxin binding by charged and uncharged resins.

It is a purpose of the present invention to provide an effective, accurate method for obtaining Gram-negative polysaccharide mixtures having low or negligable levels of endotoxin.

SUMMARY OF THE INVENTION

The invention is a process for removing endotoxin from Gram-negative polysaccharides such as polyribosylribitol phosphate (PRP) which comprises:

(a) growing Gram-negative bacteria in fermentation broth, releasing polysaccharide into the broth, and adding ethanol to the broth to remove impurities by precipitation;

(b) isolating the remaining high molecular weight species and resolubilizing them in phenol and extracting other impurities;

(c) centrifuging remaining high molecular weight species and resolubilizing in a counterion solution; and (d) adding alcohol to the solution, cooling the solution and thereafter incrementally adding alcohol to achieve lipopolysaccharide precipitation and lipopolysaccharide/polysaccharide precipitation by selective alcohol fractionation.

Preferably, the initial addition of alcohol, and temperature after cooling in step (d), result in an alcohol concentration which is up to 2%, preferably between 0.5-1% below the alcohol concentration at the cloud point. Incremental alcohol addition is preferably a sequential addition of about 0.2% at a time until a two-fold increase in turbidity occurs, at which time the cloud point has been reached. The cloud point corresponds to the percentage of alcohol present when endotoxin and polysaccharide start to precipitate, causing turbidity. After the cloud point has been reached, an additional amount of alcohol is added which results in the precipitation of most of the endotoxin with some polysaccharide and a negligible amount of endotoxin remaining in solution.

The counter ion is preferably divalent, although a monovalent counter ion may be used.

Various alcohols may be successfully used during endotoxin removal. Suitable alcohols include denatured ethanol (SDA3A, which is 4.7% MeOH, 88.1% EtOH, 7.2% $H_2O$), 95% EtOH, absolute EtOH, isopropanol, and other alcohols having 1 to 4 carbons which precipitate endotoxin.

The following abbreviations are used in the description of the present invention:

PRP - polyribosylribitol phosphate, an *H. influenzae* type b capsular polysaccharide.

LAL test value - limulus ameobocyte lysate test value, which is an indication of endotoxin level in the end-product.

LPS - lipopolysaccharide, which is the general structure of endotoxin when it is apart from the outer cell surface of Gram-negative bacteria.

EU/mcg - Endotoxin units (a measure of LPS) per microgram PRP.

BRIEF DESCRIPTION OF THE DRAWINGS

FIG. 2 Plot of alcohol at cloud point versus temperature of PRP powder solution.

FIG. 3 LAL fold reduction and percent yield.

DETAILED DESCRIPTION OF THE INVENTION

Figure 1:
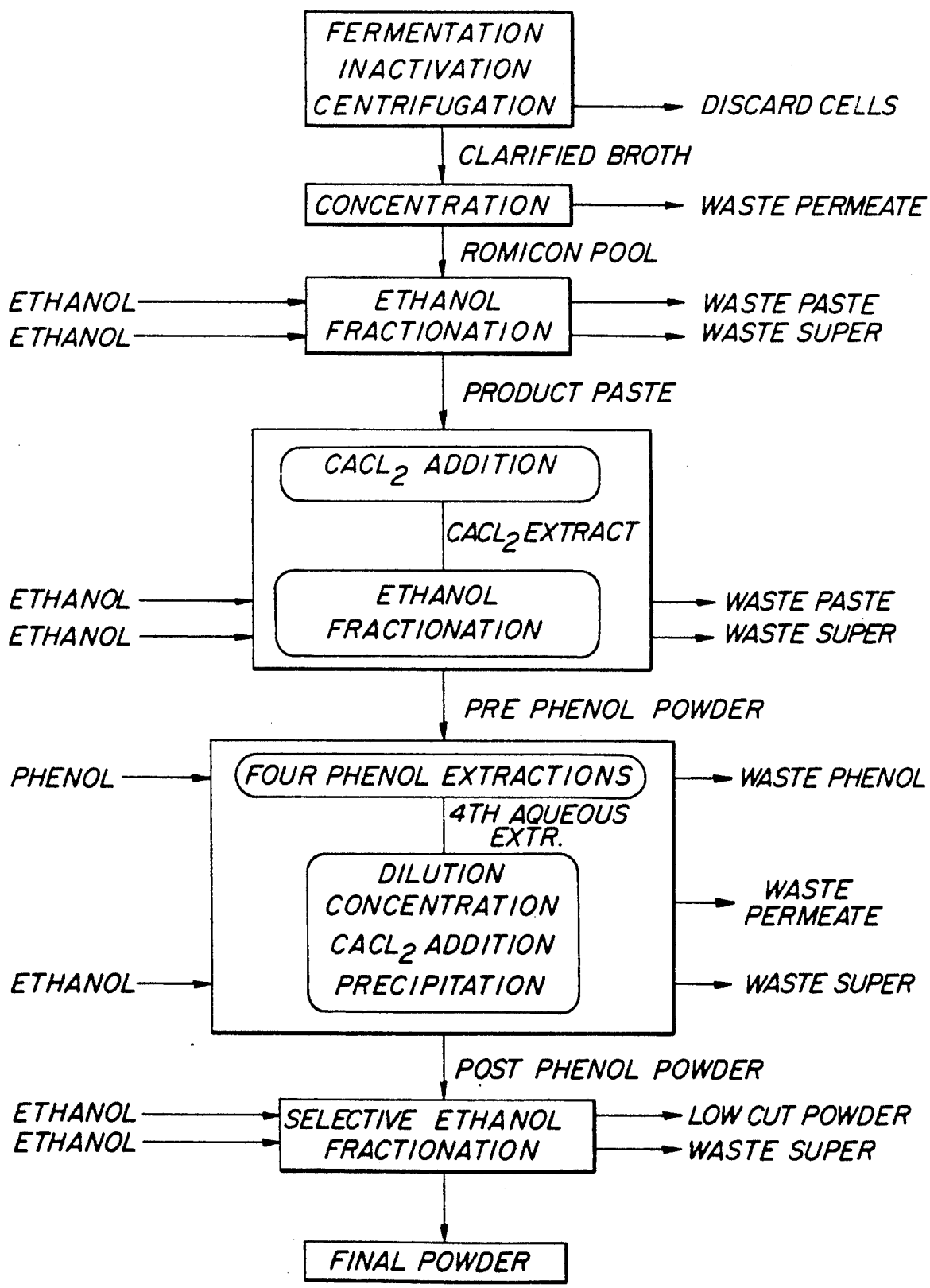
FIG. 1 Polysaccharide isolation process with selective ethanol fractionation.

The process of the present invention removes impurities such as lipids, lipopolysaccharides, proteins and nucleic acids by selective ethanol fractionation from fermentation products such as those including Gram-negative bacteria polysaccharides.

Polysaccharide solutions from which endotoxin is removed in accordance with the present invention may be those having any bacterial polysaccharides with acid groups, but are not intended to be limited to any particular types. Examples of such bacterial polysaccharides include *Haemophilus influenzae* (H. flu) type b polysaccharide; *Neisseria meningitidis* (meningococcal) groups A, B, C, X, Y, W135 and 29E polysaccharides; and *Escherichia coli* K1, K12, K13, K92 and K100 polysaccharides. Particularly preferred polysaccharides, however, are those capsular polysaccharides selected from the group consisting of H. flu b polysaccharide, such as described in Rosenberg et al., *J. Biol. Chem.*, 236, pp. 2845–2849 (1961) and Zamenhof et al., *J. Biol. Chem.*, 203, pp. 695–704 (1953).

In one embodiment of the present invention, polyribosylribitol phosphate, shown below, in the protonated form,

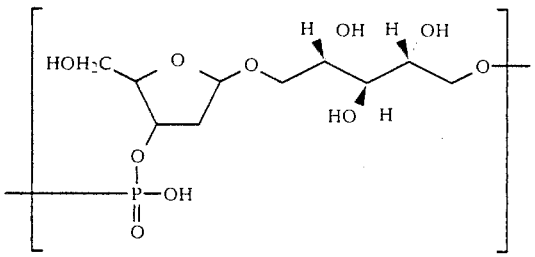

is prepared having low or negligable amounts of endotoxin. Polyribosylribotol phosphate is a polysaccharide useful for preparation of protein-polysaccharide conjugates such as those described in Marburg et al., U.S. Pat. No. 4,695,624.

A production fermenter containing complete *Haemophilus* medium with an antifoaming agent is inoculated with the seed culture. The fermenter is maintained at 37°±3° C. for a minimum of twelve hours with moderate aeration and agitation. The *H. influenzae* type b culture is inactivated after the fermentation is completed by addition of thimerosal under agitation. Cells are removed by centrifugation or filtration and discarded. The culture supernatant is concentrated by ultrafiltration and additional impurities are removed by alcohol fractionation.

The high molecular weight species precipitate is dissolved in calcium chloride solution and a minimum of one additional alcohol fractionation is completed as described above to remove additional impurities. The second alcohol precipitate is collected by centrifugation and a dry powder is obtained by resuspending the precipitate in absolute ethanol followed by filtration, acetone wash and drying.

The powder is dissolved in sodium acetate solution and extracted several times with phenol to remove impurities. The aqueous solution containing polysaccharide is diafiltered with water to remove phenol. Calcium chloride solution is added to the solution and high molecular weight species are precipitated with alcohol and collected by centrifugation. The post phenol powder is resolubilized in calcium chloride solution and is then subjected to selective alcohol fractionation.

Incremental alcohol addition is an effective process for reducing the level of endotoxin to the point where it meets product specification, while minimizing the loss of polysaccharide from solution. By changing the alcohol concentration, different molecular weight species become insoluble and precipitate out of solution. Increasing alcohol concentration precipitates species of decreasing molecular weight. When the cloud point is reached, lipopolysaccharide and polyribosylribitol phosphate begin to precipitate. Lipopolysaccharide is precipitated along with some polysaccharide, leaving polysaccharide in solution essentially unaccompanied by lipopolysaccharide. The low ethanol precipitate, which contains large quantities of lipopolysaccharides, is removed by centrifugation and discarded. Additional ethanol is added and the polysaccharide precipitate is collected by centrifugation. By following the procedure of the present invention, most lipopolysaccharide can be removed from solution before experiencing intolerable losses of polysaccharide. The resulting product is then suitable for efficient preparation of protein-polysaccharide conjugates.

Protein-polysaccharide conjugates useful for vaccination of patients against infections such as those caused by *H. influenzae* type b bacterium may be prepared using the process of the invention.

Endotoxin reduction resulting from the process of the invention is typically 30–100 fold between starting and final powder. Polyribosylribitol phosphate yield is typically at least 35% of the level in the starting material.

EXAMPLE

*H. Influenzae* Polysaccharide Isolation Process With Selective Ethanol Fractionation A schematic representation of the process followed in this example is shown FIG. 1.

*H. influenzae* type b was grown in an 800 L fermentor (640 L working volume). A sample for culture purity was obtained and the culture transferred to a kill tank where it was treated with Thimerosal. At the completion of the kill cycle (10 hours at 37° C.), the temperature was reduced and the broth held until released by the culture viability test (30 hours). The inactivated whole broth was then transferred out of the containment area, the cells and other debris removed by Sharples centrifugation, and the clarified broth stored at 2°–8° C. Since the PRP was released into the culture media, the collected cells were discarded after weighing. The dilute cell-free broth is concentrated and a first ethanol fractionation is performed to remove contaminating protein, nucleic acid and endotoxin. A second ethanol fractionation is then performed to further purify the concentrated broth, followed by a series of phenol extractions to remove residual protein, endotoxin and pigments. These fractionations and extractions result in material which contains undesirable amounts of endotoxin.

In the selective ethanol fractionation step, the lipopolysaccharide was precipitated as alcohol concentration increased, along with some polysaccharide, leaving polysaccharide in solution which was lower in lipopolysaccharide level. Preciptate containing substantial quantities of lipopolysaccharide with polysaccharide is known as the "low-cut".

Thus, the solution from which endotoxin was to be removed was cooled and a salt such as $CaCl_2$ or NaCl was added. Chilled denatured alcohol was added to achieve a concentration slightly below (about 0.5–1.0% below) the cloud point (see Graph 1). Sequential addition thereafter of about 0.2% alcohol at a time was performed until a two-fold increase in turbidity occurred, at which point the cloud point was reached.

Products obtained from Tests a, c, d, and e in Table 1 show dramatic reductions of endotoxin levels following the process of the invention. Reduction of endotoxin level is measured by measuring limulus ameobocyte lysate (LAL) test values. The test is described in "Guideline on validation of the LAL test as an end product endotoxin test for human and animal parenteral drugs, biological products, and medicinal devices". U.S. Department of Health and Human Services, December 1987. Product from Test e, which had an unacceptably high level of endotoxin, was treated a second time by selective ethanol fractionation, the results of which are shown in the product from Test f.

TABLE 1

Endotoxin Level Reduction
By Selective Ethanol Fractionation (Endotoxin Units/mcg)

| Process Stage | Test | | | | | |
|---|---|---|---|---|---|---|
| | a | b | c | d | e | f |
| Pre-phenol Powder | 750 | 650 | 530 | 600 | 780 | — |
| Post-phenol Powder | 45 | 140 | 60 | 60 | 135 | — |
| Low cut Powder | 30 | 600 | 340 | 30 | 300 | — |
| Post Selective Ethanol Fractionation Powder | 1.5 | 0.9 | 1.4 | 0.4 | 2.8 | 0.09 |

To accomplish the selective ethanol fractionation, the post-phenol powder was solubilized at 2.5 g/L in a 0.05M $CaCl_2$ solution to provide a divalent counter ion for both endotoxin and PRP. Alcohol was then added to achieve a level of 26% (v/v). After the temperature equilibrated to a constant value in the 2° to 4° C. range, alcohol was added incrementally until the PRP began to precipitate (cloud point), causing turbidity as monitored by a turbidity probe.

Graph 1 is a plot of % alcohol at the cloud point versus the temperature of a PRP powder solution. The % alcohol needed to reach the cloud point at 6° C. was 27.4% but for the 4° C. only 26.7% was required. This seemingly small increase corresponded to 700 ml for a 100 L scale run. Historical data was used to decide how much additional alcohol should be added after the cloud point was reached in order to reduce the lipopolysaccharide to meet the specification. The final powder yield decreased as the difference between Low Cut Alcohol percent and Cloud Point percent increased. Graph 2 shows that an increase in alcohol content of 1% from the cloud point alcohol concentration removed 50% of the PRP. Endotoxin reduction, as measured by LAL, was about ten fold. Therefore, alcohol addition of 1% was not sufficient to reduce the endotoxin to a level of 3 EU/mcg when the starting LAL was greater than 30 EU/mcg.

After the low cut alcohol was added, the solution was immediately centrifuged to remove low cut. Additional alcohol was added to the supernatant to 38% (v/v). The desired precipitate was collected via settling and/or centrifugation and dried to the final powder. Typical recoveries for this step using 1.2 to 2% above cloud point were 30–40% of the post-phenol powder or 13–18% of the amount from the fermentor.

The selective alcohol fractionation procedure can be repeated if the final powder does not meet the pyrogen specification. For reprocessing the product from test e, the alcohol concentration was increased 0.2% above the low cut alcohol percentage. The yield was 78% and the endotoxin level was reduced from 2.8 to 0.09 EU/mcg.

The polysaccharide product resulting from the endotoxin removal procedure of the invention is especially useful where endotoxin-free polysaccharide polyribosylribitol phosphate is desirable. It readily conjugates to proteins, e.g. immunogenic proteins, such as in the manner described in Marburg et al. (ibid). The conjugates are stable polysaccharide-protein conjugates, coupled through bigeneric spacers containing a thioether group and primary amine, which form hydrolytically-labile covalent bonds with the polysaccharide and the protein. Exemplary conjugates are those which may be represented by the formulae, Ps-A-E-S-B-Pro or Ps-A'-S-E'-B'-Pro, wherein Ps represents a polysaccharide; Pro represents a bacterial protein; and A-E-S-B and A'-S-E'-B' constitute bigeneric spaces which contain hydrolytically-stable covalent thioether bonds, and which form covalent bonds (such as hydrolytically-labile ester or amide bonds) with the macromolecules, Pro and Ps. The specific definitions of A,E,S,B,A',E' and B' are presented in Marburg et al. the contents of which are hereby incorporated by reference. Procedures for preparing polysaccharides and proteins for conjugation, performing conjugation, and determining conjugation are described in the patent.

What is claimed is:

1. A method for removing endotoxin from the outer cell of Gram-negative bacteria which comprises the steps of:
   (a) growing Gram-negative bacteria in fermentation broth, releasing polysaccharide into the broth, and adding alcohol to the broth to remove impurities by precipitation;
   (b) isolating the high molecular weight species and resolubilizing them in phenol and extracting other impurities;
   (c) centrifuging remaining high molecular weight species and resolubilizing in a counter ion solution; and
   (d) adding alcohol to the solution, cooling the solution, and thereafter incrementally adding alcohol to achieve lipopolysaccharide precipitation and lipopolysaccharide/polysaccharide precipitation by selective alcohol fractionation.

2. A method of claim 1 wherein the initial addition of alcohol and temperature after cooling in step (d) results in an alcohol concentration which is up to 2% below the alcohol concentration at the cloud point for that temperature.

3. A method of claim 2 wherein the alcohol concentration resulting from the initial addition of alcohol is between about 0.5 and 1% below the alcohol concentration at the cloud point for that temperature.

4. A method of claim 3, wherein the concentration of alcohol is repeatedly increased by about 0.2% maintaining constant temperature until the cloud point is reached.

5. A method of claim 4, wherein precipitated material is removed after the cloud point has been reached, and polysaccharide remaining in solution is dried.

* * * * *